United States Patent [19]
Ito et al.

[11] Patent Number: 5,486,479
[45] Date of Patent: * Jan. 23, 1996

[54] BUFFER FOR IMMUNOASSAY, KIT INCLUDING SAME AND IMMUNOASSAY METHOD USING SAID BUFFER

[75] Inventors: Michio Ito; Satoshi Sugawa, both of Tokyo, Japan; Atsushi Yanagida, Carmel, Ind.

[73] Assignee: Mitsubishi Chemical Corporation, Tokyo, Japan

[*] Notice: The portion of the term of this patent subsequent to May 2, 2014, has been disclaimed.

[21] Appl. No.: 235,876

[22] Filed: May 2, 1994

[51] Int. Cl.$^6$ .................................................. G01N 33/546
[52] U.S. Cl. .................... 436/533; 435/7.92; 435/7.93; 435/7.94; 435/7.95; 435/962; 436/518; 436/523; 436/529; 436/530; 436/531; 436/532; 436/822; 436/825; 436/909
[58] Field of Search ................... 435/7.92–7.95, 435/962; 436/518, 523, 529–533, 822, 825, 909

[56] References Cited

U.S. PATENT DOCUMENTS

| | | | |
|---|---|---|---|
| 4,672,045 | 6/1987 | Tsutsui et al. | 436/518 |
| 5,302,532 | 4/1994 | Lau | 436/528 |

FOREIGN PATENT DOCUMENTS

| | | | |
|---|---|---|---|
| 2042170 | 9/1980 | United Kingdom | 436/825 |
| WO90/08321 | 7/1990 | WIPO . | |

OTHER PUBLICATIONS

Chemical Abstract 108: 201346 "Quantitative Determination of Human C-Reactive Protein by Latex Agglutination Tests", Tanno et al. Kokai JP62-2188 (Jun. 6, 1988).
Chemical Abstract 108: 201348 "Reagents for Quantitative Determination of C-Reactive Protein", Tanno et al Kokai JP62,218,866 (Jun. 6, 1988).
Chemical Abstract 111: 130314 "Determination of Human C-Reactive Protein by a Latex Agglutination Test", Tanno et al. Kokai JP63,298,601 (Oct. 9, 1989).
Japanese Abstract 06–058935 "Immunoassay and Reagent Therefore" Section P, Section No. 1748 vol. 18 No. 295 p. 34 (Jun. 6, 1994).
King et al, "Evaluation of Boviac Serum Albumin Preparations . . . " Vox Sang 1991; 60 & 113–117.
Peace et al., "Cationic Antigens Problems Associated with Measurements by ELISA", J. Immunol. Methods 1986; 87: 21–27.
Polanec et al, "Evaluation of Protein Denaturing Immunoassays . . . " J. Clin. Lab. Anal. 1994; 8: 16–21.
M. E. Devey et al, "Determination of the Functional Affinity of IgG1 and IgG4 Antibodies to Tetanus Toxoid by Isotype–Specific Solid–Phase Assays," Journal of Immunological Methods, vol. 106, pp. 119–125 (1988).
M. H. Greenwood et al, "Excretion of Yersinia Spp. Associated with Consumption of Pasteurized Milk," Epideniol. Infect., vol. 104, pp. 345–350 (1990).

D. M. Hogben et al., "HBsAg: Anti–HBs Immune Complexes—A Method for Separating the Constituent Components and Assessment of the Affinity of the Antibody," Journal of Immunological Methods, vol. 93, pp. 29–36 (1986).

M. I. J. Thomas et al., "Rubella–Specific IgG1 Avidity: A Comparison of Methods," Journal of Virological Methods, vol. 31, pp. 219–228 (1991).

*Primary Examiner*—Carol A. Spiegel
*Attorney, Agent, or Firm*—Oblon, Spivak, McClelland, Maier & Neustadt

[57] ABSTRACT

The invention relates to immunoassay reagents that are both sensitive and specific and which require no sample pretreatment. The invention reagents are particularly useful for assaying digoxin concentrations in patient sera. More particularly, the invention relates to methods and kits comprising (A) an immunoreactant immobilized on a support; and, (B) a buffer agent comprising (i) a buffering agent, (ii) sodium chloride, (iii) choline chloride, (iv) a polysaccharide, (v) fatty-acid-free serum albumin, and (vi) a non-specific reaction suppressor of the formula:

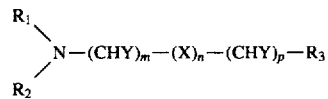

wherein X is —NH—(CO)—NH—, —NH—(CS)—NH—, or —N=C=N—, $R_1$ and $R_2$, which may be the same or different, are $C_1$–$C_5$ linear or branched alkyl groups, or $R_1$ and $R_2$, together with nitrogen, is

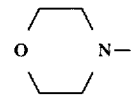

or the metho-p-toluenesulfonate salt thereof, Y, which may be the same or different, is any of H, OH and halogen, $R_3$ is —$NR_1R_2$, —$NH_2$, —CHY, cyclohexyl, or H, m is an integer of from 2 to 5, p is an integer of from 0 to 5, and n is 0 or 1, and the addition salts thereof.

19 Claims, 7 Drawing Sheets

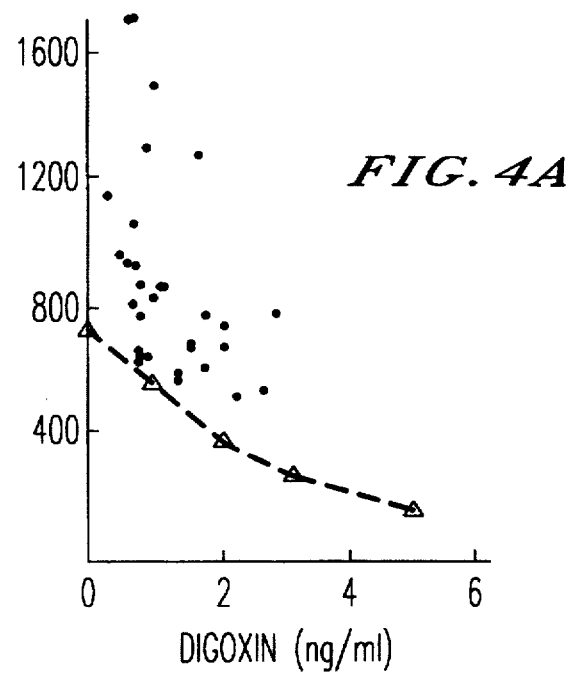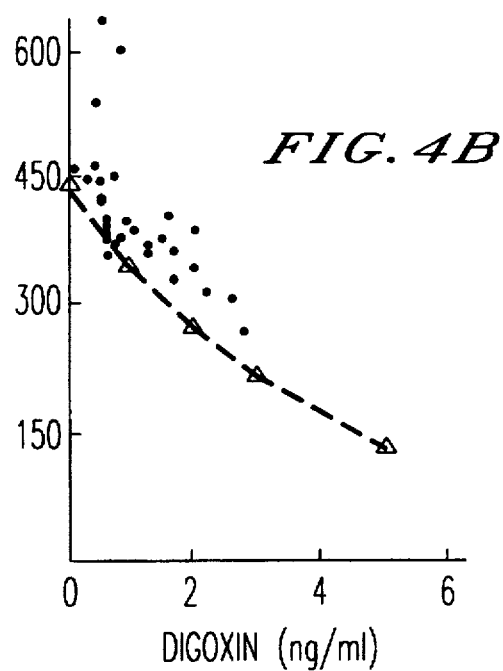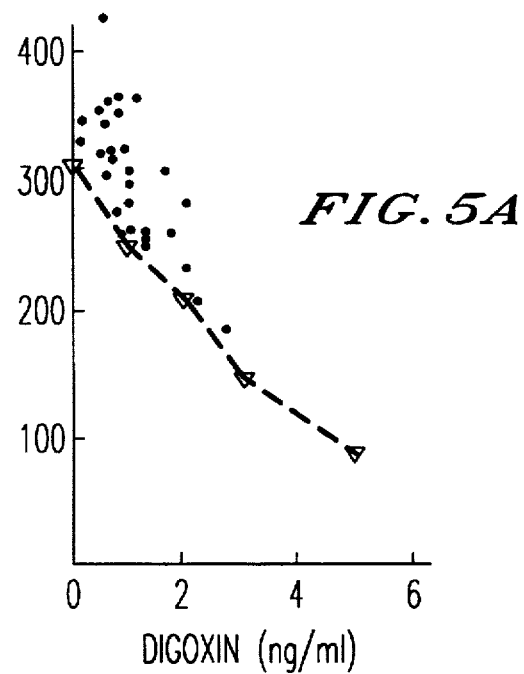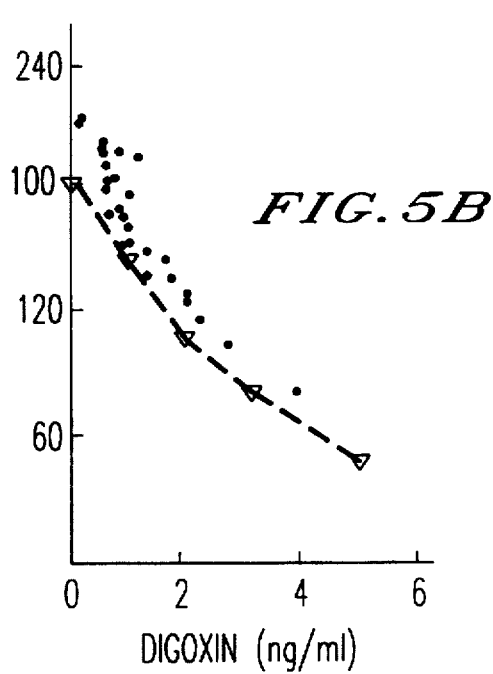

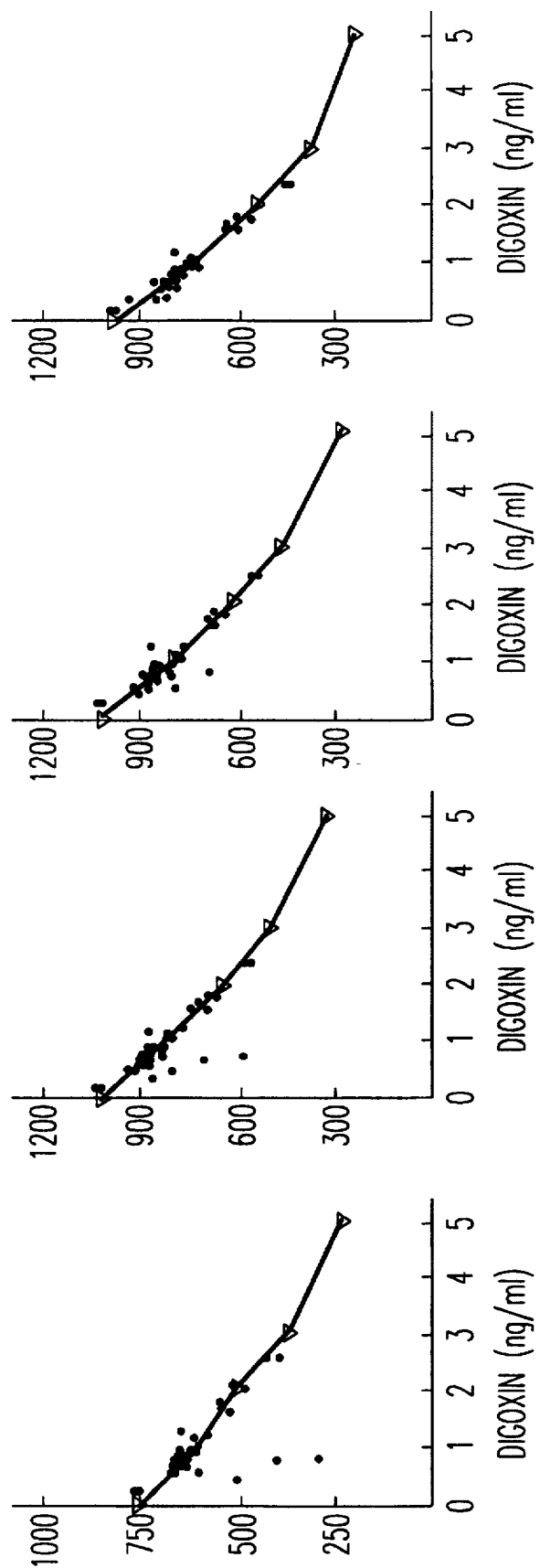

BUFFER FOR IMMUNOASSAY, KIT INCLUDING SAME AND IMMUNOASSAY METHOD USING SAID BUFFER

BACKGROUND OF THE INVENTION

1. Field of the Invention

The present invention relates to highly sensitive and specific immunoreactant assay reagents. More particularly, the present invention relates to assay reagents and systems wherein a sensitized solid reagent is provided and used in combination with a particular buffer reagent that reduces non-specific antigen-antibody reactions. The assay reagents of the present invention are designed to avoid the need for sample pretreatment and be compatible with commercial autoanalyzers typically used in the field of clinical chemistry.

2. Discussion of the Background

Digoxin is a popular cardiac glycoside currently prescribed for the control of congestive heart failure and for certain cardiac rhythm abnormalities. The increased cardiac output resulting from the ionotropic action of digoxin ameliorates the disturbances characteristic of heart failure such as venous congestion, edema, dyspnea, orthopnea and cardiac asthma. Digoxin also reduces ventricular rate and thus improves hemodynamics. Palpitation, precardial distress or weakness are relieved and concomitant congestive failure ameliorated. Digoxin also slows the heart and induces regular sinus rhythm. Regardless whether digoxin is used to control/inhibit heart failure, atrial fibrillation or flutter, the continued administration of digoxin after the onset of clinical event is typically recommended.

The therapeutic index for digoxin is very low, there being only a very narrow difference between therapeutic and toxic dosages. Digoxin levels in patients are often difficult to predict because of variation in the absorption of oral doses and the variation and non-renal excretion. Accordingly, the monitoring of serum digoxin levels is a valuable and necessary tool in decreasing patient toxicity risk and in detecting underdigitalization. This is particularly true since the incidence of toxicity increases from 5 to 71% for serum digoxin levels of 1.1 and 4.4 mg/mL, respectively.

Current digoxin immunoassay techniques include radioimmunoassay (RIA) systems, enzyme linked immunosorbent assays (ELISA) and EMIT assays. In radioimmunoassay systems, digoxin is generally labeled with radioactive iodine and the amount of labeled digoxin bound to an antibody is measured with a gamma-ray counting instrument. Such RIA systems present several drawbacks, such as the use of radioactive elements, sample instability, significant reagent preparation, expensive measuring instruments, etc.

ELISA and EMIT assays also require the labeling of digoxin, albeit with an enzyme, and the subsequent monitoring of an enzyme-substrate reaction. These assay systems, like the RIA assay, require significant reagent preparation, etc. Moreover, current assays systems typically include a serum pretreatment step in order to destroy interfering proteins which contribute to non-specific (i.e., serum interferant-digoxin antibody) reactions and lead to false positive results. For example, when performing an EMIT digoxin assay, the serum or plasma is mixed with sodium hydroxide to destroy interfering proteins.

SUMMARY OF THE INVENTION

Accordingly, one object of this invention is to provide a novel assay system which is sensitive, specific, stable and reliable and which overcomes the drawbacks of prior art assays.

Another object of the present invention is provide a highly sensitive and specific digoxin assay system.

Another object of the present invention is to provide a highly sensitive and specific assay system and kit applicable to current commercial autoanalyzers useful in the field of clinical chemistry.

Another object of the present invention is to provide a highly sensitive and specific cardiac glycoside assay system which can be operated without sample pre-treatment and which can be utilized to reliably determine the serum digoxin levels of patients simply and efficiently.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 4a and b show the effects of the concentration of sodium chloride on the invention buffer reagent in a present invention digoxin assay system.

FIGS. 5a and 5b show the effects of the concentration of choline chloride on a digoxin assay according to the present invention.

FIGS. 6a–d show the effect of fatty-acid-free human serum albumin (HSA) on a digoxin assay system according to the present invention.

DESCRIPTION OF THE PREFERRED EMBODIMENTS

Figure 1A:
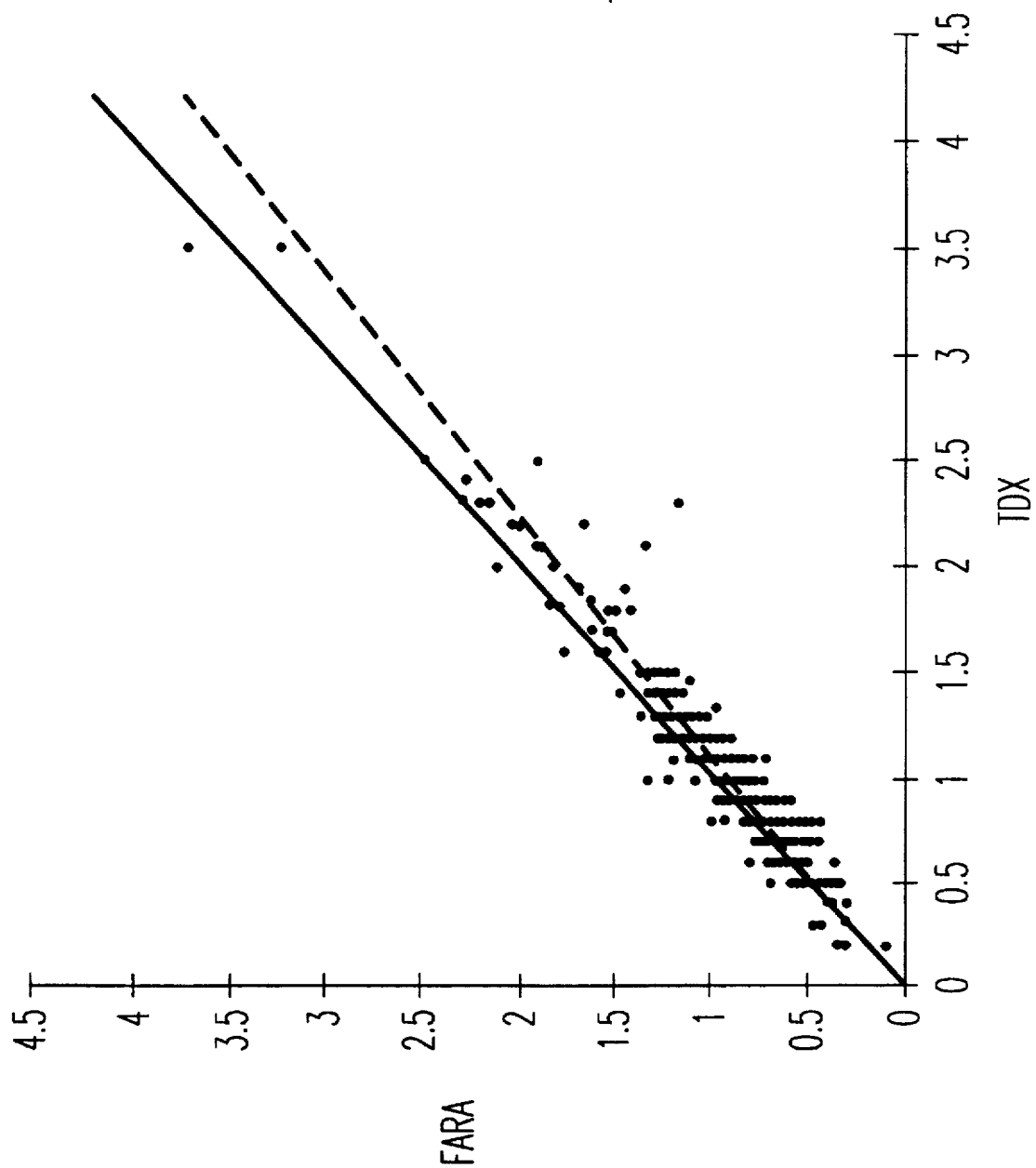
FIGS. 1a–d show the results obtained with a present invention digoxin assay system (Y axis) as a function of the results obtained with the Abbot TDx® method (X axis).

The present invention is directed to an immunoassay system and immunoassay reagents capable of determining the presence and amount of a desired species in a sample. These reagents include a solid support having, on the surface thereof, an immunoreactant (i.e., a sensitized support), and a buffer reagent comprising buffering components, sodium chloride, choline chloride, fatty-acid-free serum albumin, a polysaccharide like sodium detran-sulfate or methyl cellulose, optionally a complimentary immunoreactant and, optionally, a secondary or tertiary amine non-specific reaction suppressor. Kits with two container means, one containing the sensitized solid support and the other containing the buffer components, are also provided. Any container means can be used, including vials, jars, tubes, bottles, foil packs, etc. Removably-sealed and unsealed containers can be used. The container means and sealing means can be made from any material such as glass, plastic, metal, composite, etc.

The invention reagents can be used in any immunoassay system or method which utilizes a solid support which has been sensitized with an immunoreactant and a buffer reagent. Several immunoassay methods and automated and semi-automated devices in which the present invention reagents may be used are described and explained in the *Handbook of Experimental Immunology*, vols. 1–4, Blackwell Scientific 1987, in U.S. Pat. Nos. 3,088,875, 3,857,931, 3,992,517, 4,080,264, 4,174,952, 4,203,724, 4,480,042, 4,590,156, 4,690,906, 4,716,123, 4,772,550, 4,851,329, 4,960,692 and 5,100,805, and in Grange, J. et al., *J. Immuno. Meth.*, 18,365,1977, Hechemy, K. et al., *Lab Management*, 27 June/July 1984, Looney, C., *J. Clin. Immunoassay*, 7,(1), 90, 1984, Von Schulthes, G. et al., *Mol Immunol*, 1, 81, 1980, Craine, J., *Am. Biotech, Lab.*, 34, May-June, 1987, Heveran, J., *J. Forensic Sci.*, 470, 1977 and Kimura, H. *J. Immuno. Meth.*, 38, 353, 1980, all incorporated herein by reference. Competitive and noncompetitive methods are included.

Preferably, a particle-based immunoassay system is utilized with the present invention immunoassay reagents, and immunoassay systems based upon latex agglutination or latex agglutination inhibition are most preferred (see U.S. Pat. Nos. 4,203,724 and 5,100,805, and *J. Clin. Chem.* 38(b), 1012 (1992), all three incorporated herein by reference). Analyzers useful for conducting immunoassays using the present invention reagents and methods include the LPIA-100 fully automated latex immunoassay system of Mitsubishi Kasei Corporation, Japan, the COBAS FARA and COBAS MIRA systems of Roche Diagnostic Systems, Inc. and the Hitachi 704 analyzer.

When using latex particle agglutination or agglutination inhibition methods, any quantitative photometric instrument which has the capability of dispensing the sample and, optionally, an antibody reagent, into a cuvette to allow pre-incubation followed by the dispensing of a sensitized solid reagent into the cuvette and monitoring the ensuing reaction photometrically is preferred. Of course, any instrument capable of measuring agglutination or agglutination inhibition by, e.g., light scattering techniques, etc. can be used and sample addition, reagent addition, etc. can be conducted by hand or by semi-automated methods.

Any solid substrate useful in immunoassays can be utilized for preparing the invention immunoreactant-sensitized solid support reagent. Examples include silica surfaces, agarose gels, etc. Preferred sensitized reagents are latex-based microparticles. These latex-based microparticles may optionally be surface carboxylate-modified and have a diameter of from 0.020–0.75 μm, preferably 0.1–0.6μm, most preferably 0.18–0.5μm. Particularly useful diameters include 0.18, 0.20, 0.25, 0.30, 0.35, 0.40, 0.45 and 0.50 μm. If the latex-based particle used in the present invention is carboxylate-modified it preferably has a 4–40, more preferably 8–35, most preferably 10–30 square A carboxylate surface parking area (i.e., the surface area of the particle divided by the total number of $COO^-$ and $COOH$ functional groups on the surface thereof). Certain preferred latex particles are described by the present inventors in copending U.S. Ser. No. 08/235,785 filed Apr. 29, 1994 entitled Microparticle Immunoassay Reagents incorporated herein by reference.

The most preferred latex-based particles useful in present invention are any carboxylate-modified polymeric or copolymeric particles which are made by any technique known in the art, including emulsion polymerization, seeded emulsion polymerization and, preferably, suspension polymerization. The particles may be made with or without a crosslinking agent and include particles of a core-shell type. Any polymeric particle having sufficient surface carboxylate groups may be used as a preferred embodiment of the present invention.

Useful latex-based particles include those made from $C_1$–$C_8$-, preferably $C_1$–$C_2$-(meth)acrylates which have been carboxylate-modified and carboxylate-modified polystyrene.

Methods for preparing carboxylate-modified latex microparticles useful in the present invention are known in the art and are described in, e.g., U.S. Pat. Nos. 5,015,695, 4,988,770, 4,978,719, and 4,962,154, all incorporated herein by reference. It is preferred that the invention latex-based microparticle reagent described above be substantially spherical, preferably completely spherical, and preferably monodisperse. The surface parking area of the invention microparticle, when carboxyl-modified, is calculated by the overall diameter and number of carboxyl groups determined by, e.g., titration.

The invention solid support carries an immunoreactant on the surface or in the pores thereof so as to provide a sensitized solid reagent, preferably a sensitized latex-based microparticle reagent. The immobilization of immunoreactants on solid supports is well known in the art and described in e.g., *Immobilized Affinity Ligand and Techniques*, G. T. Hermanson, et al, 1992, U.S. Pat. Nos. 4,203,724, 4,716, 123, 4,772,550, 4,851,329, 4,960,692 and 5,100,805, 4,045, 384, 4,140,662 and 4,680,338, in Quasla, G. et al., *J. Immuno. Meth.*, Vol. 22, 165, 1978, Srere, P. et al., *Meth. Enzym.*, 44, 11, 1976, Nustad, K. et al., *Devel. Biol. Stds.* 57, 321, 1984, Bahadur, A. et al, *Makromol. Chem.*, 186, 1387, 1985, Margel, S. et al., *J. Immuno. Meth.* 28, 341, 1979, and Suen, C. et al., *Makromol. Chem.* 186, 255, 1985, all incorporated herein by reference. Covalent attachment, adsorption, absorption, etc. are useful. Linker molecules like those described in the Pierce *Immunotechnology Catalog and Handbook*, Pierce Chemical Company, 1992, incorporated herein by reference, can be used as can mixtures of immunoreactants. A preferred method for attaching the invention immunoreactant to the invention solid support, and to the preferred latex-based particle is through covalent bonding via the use of a carbodiimide coupling reagent. The use of carbodiimide coupling reagents to effect the condensation of a carboxylic acid functionality with an amine is well-known in the art and described in *Organic Chemistry* by Streitweiser and Heathcock, MacMillan, 1976, by Sheehan, J. C., et al., in *J. Amer. Chem. Soc.* 95, 875 (1973), by Thomas, J. O., et al., in *J. Mol. Biol.*, 123, 149 (1978), by Packer, L., et al., in *FEBS LETT.*, 108, 243 (1979), in *Anal. Biochem.*, 63, 485 (1975), in *Plant Physiol.*, 53, 619 (1974), and in *J. Org. Chem.*, 21, 439 (1956), all incorporated herein by reference.

Particularly preferred carbodiimide coupling reagents for condensing solid support surface groups to the immunoreactant include dicyclohexylcarbodiimide (DCC), 1-ethyl-3-(3-dimethylaminopropyl)-carbodiimide (EDC) and 1-cyclohexyl-3-(2-morpholinoethyl)carbodiimide (CMC). EDC is particularly preferred due to its high solubility, effectiveness under mild conditions and ease of reaction control.

The total amount of immunoreactant adsorbed, covalently bound, etc. to the invention solid support varies with the support characteristics, immunoreactant, desired binding rate, etc. For example, for the preferred carboxylate-modified latex-based microparticles 50–10,000, preferably 200–2000, immunoreactant molecules are covalently bound thereto.

Typically, the amount of carbodiimide used to effect coupling is from 0.01 to 5 percent of the weight of the particles, preferably 0.05 to 2 percent, or 2–5 times the equivalence of the latex surface carboxylate groups. See U.S. Pat. Nos. 4,181,636 and 4,045,384 incorporated herein by reference.

Carbodiimide-catalyzed coupling of carboxyl groups to amino groups can produce undesirable by-products which can provide reaction sites for non-specific reactions. In order to counter the formation of such by-products, an excess amount of an amine can be added after the coupling reaction has progressed sufficiently, and any carbodiimide-modified surface carboxylate residue can be returned to an acid or a carboxylate functionality through the use of an amino acid. In this manner, the surface charge of the invention microparticle reagent remains relatively constant and controllable. Preferred amines useful for quenching the carbodiimide coupling reaction include ethanolamine, ethylenediamine, glucosamine, glycine and lysine. Glycine and lysine are preferred, and glycine is particularly preferred.

Prior to effecting coupling of the immunoreactant to the preferred latex-based particle it is preferred to clean the microparticle by, e.g., passing the particle through an ion exchange resin such as Bio-Rad mixed bed resin AG 501-X8.

The immunoreactants useful in the present invention are those which undergo specific reaction with a complimentary immunoreactant in any type of immunoassay system including direct and competition assays, sandwich assays, agglutination assays, etc. As used herein, the term immunoreactant means any antigen or antibody optionally covalently, etc., attached to other molecules such as proteins or synthetic or natural polymers, etc., and the term complementary immunoreactant means any antibody or antigen optionally covalently, etc., attached to other molecules such as synthetic or natural polymers, etc. capable of specifically binding to the immunoreactant. As used herein, the immunoreactant is the species bound, absorbed or adsorbed on the solid reagent and the complementary immunoreactant is the species which specifically reacts with the immunoreactant. The specie being measured can thus be either an immunoreactant or complimentary immunoreactant depending upon the type of assay employed: i.e., depending on what is bound to the solid support, what, if anything, is present in solution, and how the assay behaves (competition, direct, sandwich, etc.).

Examples of immunoreactants and complementary immunoreactants useful in the present invention include the following:

| | |
|---|---|
| AFP | Alpha-fetoprotein |
| Beta-2-microglogulin | |
| CEA | Carcinoembryonic antigen |
| Ferritin | |
| CA 19-9 | Carbohydrate antigen 19-9 |
| PAP | Prostatic acid phosphatase |
| PSA | Prostate-specific antigen |
| CRP | C-reactive protein |
| Mb | Myoglobin |
| RF | Rheumatoid factor |
| ASO | Anti-streptolysin-O |
| FDP | Fibrin degradation product |
| Anti-thrombin-III | |
| Plasminogen | |
| Alpha-2-plasmin inhibitor | |
| D-dimer | Fibrin degradation product D-fragment dimer |
| IgG | Immunoglobulin G |
| IgA | Immunoglobulin A |
| IgM | Immunoglobulin M |
| IgE | Immunoglobulin E |
| C3 | Complement 3 |
| C4 | Complement 4 |
| Urinary albumin | |
| hCG | human chorionic gonadotropin |
| hPL | Human placental lactogen |
| Insulin | |
| HBs antigen | Hepatitis-B surface antigen |
| HBs antibody | Anti-hepatitis-B core antigen antibodies |
| HBc antibody | Anti-hepatitis-B core antigen antibodies |
| HCV antibody | Anti-hepatitis-C virus antibodies |
| Treponema | Anti-treponema pallidum antibodies |
| TSH | Thyroid stimulating hormone |
| LH | Lutenizing hormone |
| FSH | Follicle stimulating hormone |
| Digoxin | |
| Digitoxin | |
| Quinidine | |
| Procainamide | |
| NAPA | N-acetyl procainamide |
| Theophylline | |
| Phenytoin | |
| Phenobarbitol | |
| Carbamazepine | |
| Valproic acid | |
| Ethosuccimide | |
| Gentamicin | |
| Tobramycin | |
| Amikacin | |
| Vancomycin | |
| Cyclosporin-A | |
| B12 | Vitamin B12 |
| Folic acid | |
| T3 | Triiodothyronine |
| T4 | Thyroxine |
| Estrogen | |

All of the above-identified species can be called either an immunoreactant or a complementary immunoreactant depending on their role in a given immunoassay. Pairing is important, the name is not, and where only an immunoreactant is referred to herein any of the above species and similar known species are meant. Naturally, all immunoreactants complimentary to those listed above are included in the present invention. As mentioned above, protein conjugates such as HSA and bovine serum albumin (BSA) conjugates of haptens are included in the invention immunoreactants. Specific examples of such carrier-hapten conjugates include digoxin-HSA and digoxin-BSA. Methods for producing conjugates are explained in Erlanger, B. *Meth. of Enzym* 70, 85, 1980 and Bauminger et al., *Meth. in Enzym.*, 70, 151, 1980, both incorporated herein by reference. Other immunoreactants and complimentary immunoreactants useful in the present invention are described in the Pierce *Immunotechnology Catalogue and Handbook*, Pierce Chemical Company, 1992, incorporated herein by reference.

In a preferred embodiment of the present invention, the immunoreactant-sensitized (hereinafter referred to simply as "sensitized") solid support is a carboxylate-modified latex-based microparticle reagent having an immunoreactant covalently bound to the surface thereof via a condensation reaction in the presence of a carbodiimide. However, any method known in the art for covalently attaching immunoreactants to carboxylate groups may be used.

The buffer reagent of the present invention comprises buffering agents, sodium chloride, choline chloride, a polysaccharide compound such as one or both of sodium dextransulfate and methyl cellulose, optionally a complimentary immunoreactant which specifically reacts with the immunoreactant on the invention sensitized support, fatty-acid-free serum albumin and, optionally, a secondary or tertiary amine non-specific reaction suppressor.

The invention antibody buffer reagent is preferably water-based and has a pH of from 4.5 to 10, preferably 5.5 to 9.5.

The amount of sodium chloride present in the buffer may vary from 1.0 to 5, preferably 1.5 to 4.5, most preferably 2.0–4.0 wt %. The amount of choline chloride present in the invention reagent buffer is from 1 to 15%, preferably 2–12%, most preferably 4–8% by weight. Typical pH buffering agents (the term "a buffering agent" means those single substances or combination of substances which resist a change in hydrogen ion concentration upon the addition of acid or alkali) are used in the present invention antibody buffer reagent. Examples include Tris-(hydroxymethyl)-aminomethane, phosphate buffering agents, those listed in the Pierce *Immunotechnology Catalogue and Handbook*, etc. The weight percentages above and below are based on the total buffer weight.

The present invention buffer reagent also includes at least one polysaccharide like sodium dextransulfate, methyl cellulose, etc. Other examples include carboxymethylcellulose, dextran, etc. The polysaccharide thickens the buffer reagent to an acceptable viscosity. Typically, the amount of sodium dextran sulfate useful in the present invention buffer reagent is from 0.2–3.0, preferably 0.6–2.0, most preferably 1.0–1.8 weight percent. The amount of methyl cellulose useful in the present invention buffer reagent is from 0.05–1.0, preferably 0.1–0.4, most preferably 0.15–0.3% weight percent.

The fatty-acid-free serum albumin useful in the present invention is characterized in that it is substantially free of fatty acids. This material can be prepared by the method of Chen, R. J., *J. Biol. Chem.*, 242,173 (1967), incorporated herein by reference and may be commercially obtained in varying species and grades from Sigma and Miles. Human, bovine, rabbit, sheep, etc. serum albumins can be used. The amount of fatty-acid-free serum albumin useful in the present invention buffer is from 5–100, preferably 7.5–60, most preferably 10–40 mg/ml of buffer. Fatty acid free human serum albumin is most preferred. Materials that are fatty acid free and globulin free are also preferred.

The optional complimentary immunoreactant useful in the present invention buffer reagent is any complimentary immunoreactant which specifically reacts with the immunoreactant used to sensitized the above-described sensitized solid reagent. This species is optional since, e.g., in direct immunoassay in which the species in the sample being detected or quantitated reacts directly with the sensitized solid support no complimentary immunoreactant in solution is necessary. When used, preferred complimentary immunoreactants are monoclonal antibodies which specifically react with the immunoreactant used to sensitized the solid reagent. Anti-digoxin monoclonal antibodies are particularly preferred. Methods for producing monoclonal antibodies are well known in the art and are described in D. E. Yelton et al, *Annu. Rev. Biochem.*, 50, 657, 1981, Milstein, C., *Sci. American*, 243(4), 66, 1980; Kennett, R. H. et al. *Monoclonal Antibodies*, Plenum Press, New York, 1980 and Kohler, G. et al, *Nature*, 256, 495 (1975), all incorporated herein by reference.

As described above, an optional component of the invention buffer reagent is one or more of a secondary or tertiary amine which improves the accuracy and reliability of the invention immunoassay reagents and methods by significantly reducing or eliminating non-specific interactions. These secondary and tertiary amines may be used singly or in addmixture, and are described in copending U.S. Ser. No. 08/194,475, incorporated herein by reference. The secondary and tertiary amine non-specific reaction suppressors useful in the present invention are those of the formula:

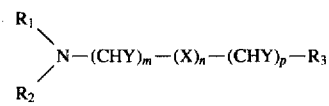

wherein X is —NH—(CO)—NH—, —NH—(CS)—NH—, or —N=C=N—, $R_1$ and $R_2$, which may be the same or different, are $C_1$–$C_5$ linear or branched alkyl groups, or $R_1$ and $R^2$, together with nitrogen is

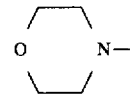

or the metho-p-toluenesulfonate salt thereof,

Y, which may be the same or different, is any of H, OH and halogen (such as Br, Cl, F, etc.), $R_3$ is —$NR_1R_2$, —$NH_2$, —CHY, cyclohexyl, or H, m is an integer of from 0 to 5, p is an integer of from 0 to 5, and n is 0 or 1, provided that at least one of m and p is at least 1 when n equals 1, and provided that when m=n=p=0, $R_3$ is H or —$CH_2Y$, and the acid addition salts thereof, particularly the HCl salts, phosphoric acid salts and sulfuric acid salts thereof. A preferred group of suppressors are those where m is at least 1 when n=1.

These secondary and tertiary amines including N,N-dimethylethylamine and dimethylaminopropylchloride and may be substituted on any or all of the m and p methylenes with any combination of H, OH and halogen, include compounds where m=n=p=0 and $R_3$ is, e.g., H or methyl, compounds where m, optionally n and optionally p are not 0 and $R_3$ is H or —$CH_2Y$, etc.

Several of the above-described compounds are the hydrolysis products of carbodiimides useful in the preparation of peptides. See Sheehan, J. C., et al, *J. Org. Chem.*, 26, 2525, 1961 and Staros, J. V., et al, *Anal. Biochem.*, 156, 220, 1986, both incorporated herein by reference. One particularly preferred non-specific reaction suppressor is 1-ethyl-3-(3-dimethylaminopropyl)urea (EDU), i.e., a compound according to the formula above where $R_1$=$R_2$=methyl, Y=H, m=3, n=1, p=1 and $R_3$=methyl. Another is 1-cyclohexyl-3-(2-morpholinoethyl) carbodiimide metho-p-toluenesulfonate (CMC). These compounds and their hydrolysis products are useful for suppressing non-specific reactions in immunoassay, particularly immunoassay wherein an immunoreactant is attached covalently or by adsorption to a solid support.

The invention non-specific reaction suppressors are generally commercially available and prepared by simple organic reactions well known to those of ordinary skill in this art and explained in, e.g., *Introduction to Organic Chemistry*, A. Streitwieser and C. Heathcock, Macmillan, 1976; *Reagents for Organic Synthesis*, Feiser and Fieser, John Wiley and Sons, 1967 and succeeding volumes; *Survey of Organic Syntheses*, John Wiley and Sons, Vols I and II, 1970; and *Advanced Organic Chemistry*, March, Wiley, 1985, all incorporated herein by reference. For example, the urea compounds (—NH—CO—NH—) can be prepared by hydrolysis of the carbodiiminde (—N=C=N—) compounds.

The non-specific reaction suppressor of the present invention described by the above formula may be used singly or in combination and may be added to the invention buffer reagent or adsorbed on the invention sensitized solid support before or after sensitization. Further, the non-specific reaction suppressor can be utilized in combination with conventional non-specific reaction suppressors.

A particularly preferred embodiment of the present invention is one where a compound according to the above formula is used to suppress non-specific immunoassay reactions in a system in which an immunoreactant has first been bound to a solid substrate using a carbodiimide reagent such as 1-ethyl-3-(3-dimethylaminopropyl)-carbodiimide hydrochloride (EDC) or CMC. A further preferred embodiment of the present invention is one where the non-specific reaction suppressor utilized is the hydrolysis product of the carbodiimide used in the binding of the immunoreactant to the solid support.

Wide ranges of suppressor concentration are effective. In general, the amount of non-specific reaction suppressor useful for suppressing non-specific immunoassay reactions according to the invention is from 0.1 to 300 mM, preferably 0.5 to 50 mM, more preferably 1.25 to 25 mM based on the total immunoassay solution volume, the total buffer volume, the solution volume of a sample to be tested, or on the solution volume of a solid support sensitized with immunoreactant suspended in a solvent.

The sensitized solid reagents and buffer reagents of the present invention allow for highly sensitive and specific immunoassay determinations. When used in a direct-measurement (i.e., non-inhibition mode) assay the complimentary immunoreactant is omitted from the invention buffer composition, and only sodium chloride, choline chloride, polysaccharide, fatty-acid-free serum albumin and, optionally, one or more of the secondary or tertiary non-specific reaction suppressors are used with conventional buffering ingredients. When an assay based on inhibition is used a complimentary immunoreactant is present in the invention buffer reagent and the sample to be tested is contacted with the buffer reagent and incubated for from 1–20 minutes. Upon completion of incubation the sensitized solid reagent is added to the mixture to bind unoccupied complimentary immunoreactant binding sights, and the rate of binding is inversely related to the immunoreactant concentration in the serum sample.

The present invention immunoassay reagents, immunoassay systems, and methods comprising them provide highly sensitive and specific determinations of specie concentration in samples, particularly patient serum samples. For example, an immunoassay system based upon latex agglutination inhibition and utilizing the preferred invention latex-based digoxin-HSA sensitized microparticle reagent and an antibody buffer reagent comprising sodium chloride, choline chloride, sodium dextran-sulfate or methyl cellulose, an anti-digoxin monoclonal antibody, fatty-acid-free serum albumin and e.g., 1-ethyl-3-(3-dimethyaminolpropyl)-urea provides a precise and reliable assay system for determining the amount of digoxin in patient sera. This is particularly true for all the invention reagents and for the preferred reagents when the volume of the serum or plasma specimen used is less than 4% of the total immunoassay system volume, and can be accomplished without any special sample pre-treatment such as deproteination, resin treatment, ultra filtration, etc.

When the reagents of the present invention are utilized with automated, e.g., photometric, instruments commercially available and having the capability of dispensing both sample and buffer (optionally containing a complimentary immunoreactant) into a cuvette and dispensing a solid sensitized reagent into the cuvette with mixing one can quantitate the amount of sera immunoreactant for large numbers of patient samples in a short amount of time with excellent reliability and sensitivity.

The superior results afforded by the present invention reagents and immunoassay systems and methods using them (both general and preferred embodiments) are derived from several aspects of the above-described invention including the use of the fatty-acid-free serum albumin in the buffer reagent (and/or pre-applied on the solid sensitized reagent if desired) and the optional use of the secondary or tertiary non-specific reaction suppressors in the buffer reagent (and/or absorbed on the solid sensitized reagent, if desired). Due to the sensitivity of the present reagents and methods using them, small amounts of sample may be used while maintaining accuracy and reliability. Conventional immunoassay reagents and methods sacrifice sensitivity when sample volume is reduced: the present invention reagents and immunoassay using them maintain high sensitivity even at low sample volume.

The following examples serve to further explain the present invention. The present invention is not limited to these Examples, however.

EXAMPLES

Preparation of Latex-based Microparticle

A 10 gallon glass lined reactor fitted with a condenser and stirrer was charged with 83 gms of sodium bicarbonate, 14,000 gms of deionized water and a surfactant (224 gms of MA- 80). This mixture was heated to 160° F. and purged with argon for 10 minutes. 208 gms of acrylic acid and 11,200 gms of styrene were mixed together and purged with argon and charged on top of the aqueous phase. The resulting emulsion was allowed to equilibrate 10 minutes.

33.6 gms of potassium persulfate was dissolved in 2000 gms deionized water, purged with argon and charged to the glass lined reactor to initiate polymerization. After 8 hours the reactor was cooled and discharged to obtain 28,000 gms of a 40% by weight suspension of 0.138 μm carboxylate-modified microparticles. Conductiometric titration showed 0.931 milliequivalents per gram of weak acid.

Preparation of Digoxin Reagents

1. Conjugate preparation

A digoxin-HSA conjugate was prepared according to the modified methods of Smith, T. W., et al., *Biochemistry*, 9, 331 (1970) and Bulter, U. P. et al, Proc. Natl. Acad. Sci. U.S., 57, 71 1967, both incorporated herein by reference. A representative protocol is as follows:

To 0.5 g of digoxin (obtained from Sigma) suspended in 20 ml of absolute ethanol at room temperature was added 20 ml of 0.1M sodium metaperiodate dropwise with stirring. After 25 minutes, 0.6 ml of 1M ethylene glycol was added. Five minutes later, the reaction mixture was added dropwise with stirring to 0.6 g of human serum albumin (obtained from Sigma) in 20 ml of 9.5 pH water (adjusted with $K_2CO_3$). The pH of the aqueous solution was maintained in the range of from 9.0–9.5 by the dropwise addition of 5% $K_2CO_3$. After 45 minutes, the pH was stable and 0.3 g of sodium borohydride freshly dissolved in 20 ml of water was added thereto. Three hours later, 7.6 ml of 1M formic acid was added to lower the pH to 6.5 and, after 1 hour, the pH was raised to 8.5 by the addition of $NH_4OH$. The entire reaction mixture was dialyzed against cold running tap water for 4 days and finally dialyzed against 0.1 M $NaHCO_3$ including 0.05% $NaN_3$ and kept in a refrigerator.

2. Sensitized microparticle reagent preparation

A) Ion exchange treatment of latex particle:

To 100 ml of a carboxylate-modified latex particle suspension (10% solids; 0.292 µm diameter; 0.31 meq carboxylate/g, 10.5 square angstrom parking area, particle made by Seradyn, Inc. is added 20 g of a mixed-bed ion exchange resin (BioRad AG 501-X8) with slow stirring for 2 hours at room temperature. The suspension is then filtered using glass fiber filters to remove the resin, and the latex is ready for coupling.

B) Latex particle coupling reaction for digoxin-HSA conjugate:

To a 50 ml polycarbonate centrifuge tube is added 15 ml of 0.1M bicarbonate buffer, pH 8.0, and 5 ml of the above cleaned 10% solids latex suspension, and then incubated at 37° C. for 10 min with stirring prior to reaction. 5 ml of 88 mg/ml 1-ethyl-3-(3-dimethylaminopropyl)-carbodiimide hydrochloride (EDC; freshly dissolved with water) is added to the mixture to activate carboxyl residues on latex surface for 10 min. After activation, 2.5 ml of 10 mg/ml of the above digoxin-HSA conjugate is added with vigorous stirring and incubated for 10 min. The reaction is stopped by adding 5 ml of 500 mM glycine buffer, pH 8.5. Another 10 min incubation is done to ensure complete termination.

C) Washing of the conjugate coupled (i.e., sensitized) latex reagent:

The digoxin-HSA conjugate coupled latex particles are centrifuged at 26,000×g for 20 min. The supernatant is discarded, and to the pellet is added 25 ml of water. The pellet is then resuspended by vigorous stirring and washing is repeated four times; however, in the last resuspension, 0.05% sodium azide solution is used as storage medium. Finally, the latex suspension is sonicated and diluted to the concentration (normally 0.1–0.4% solids) ready for use.

3. Preparation of Anti-digoxin Antibody Buffer Reagent Composition

A digoxin antibody reagent was prepared by dissolving the following materials in water and adjusting the pH with hydrochloric acid. The antibody was added last.

| | |
|---|---|
| 4.375% | NaCl |
| 250 mM | Bis-Tris, pH 6.5 |
| 6.4% | Choline Chloride |
| 1.25–1.75% | Sodium Dextransulfate |
| 2.0% | Fatty-acid-free human serum albumin (FAF-HSA) |
| 25 mM | 1-Ethyl-3-(3-dimethylaminopropyl)- |
| | urea |
| 0.1% | Sodium azide |
| 0.01% | Antifoam 1410 (Dow Corning) |
| 1:86,000–120,000 | Diluted anti-digoxin monoclonal antibody |

Assay Parameters for Chemistry Analyzers

| Instrument name | COBAS FARA | COBAS MIRA | HITACHI704 | LPIA100 |
|---|---|---|---|---|
| Wavelength | 750 nm | 600 nm | 700 nm | 650 or |
| Temperature | 37° C. | 37° C. | 37° C. | 37° C. |
| Sample volume | 6 ul | 6 ul | 15 ul | 10 ul |
| Antibody reagent | 120 ul | 120 ul | 220 ul | 200 ul |
| Latex reagent | 25 ul | 20 ul | 160 ul (3x diluted) | 40 ul |
| Pushing Water/Buffer | 20 ul | 35 ul | — | 50 ul |
| Sample/Antibody Preincubation | 10 min | 7 min | 5 min | 10 min |
| Reading Time | 5 min | 4 min | 5 min | 10 min |

Example 1

Figure 1B:
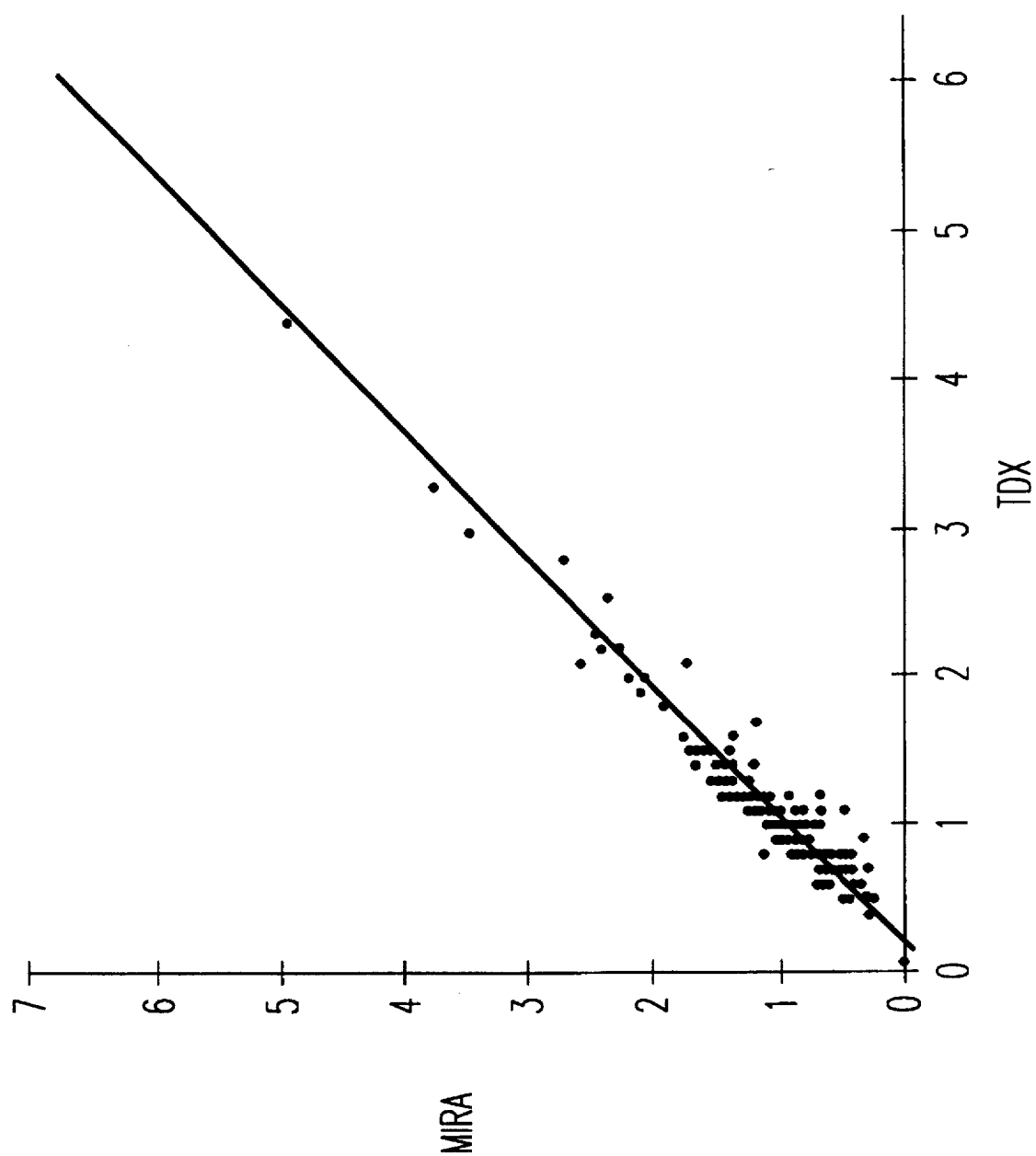
Figure 1C:
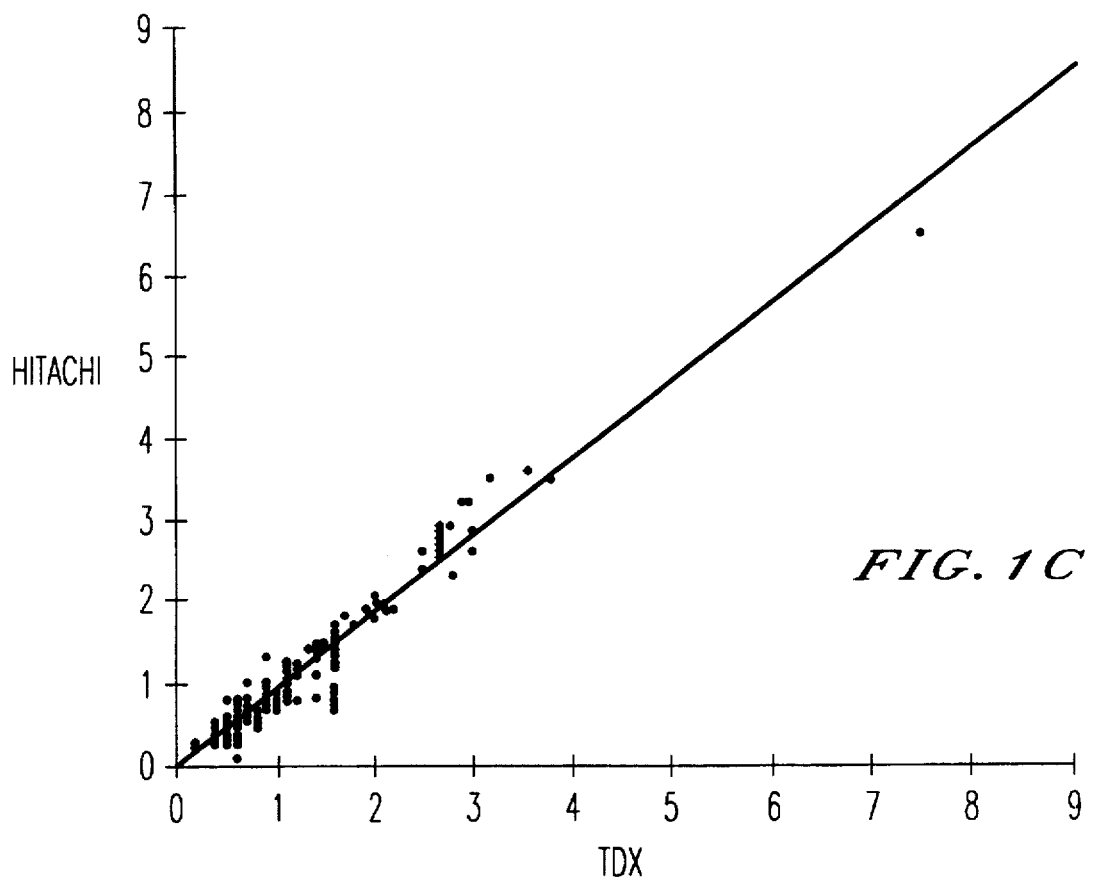
Figure 1D:
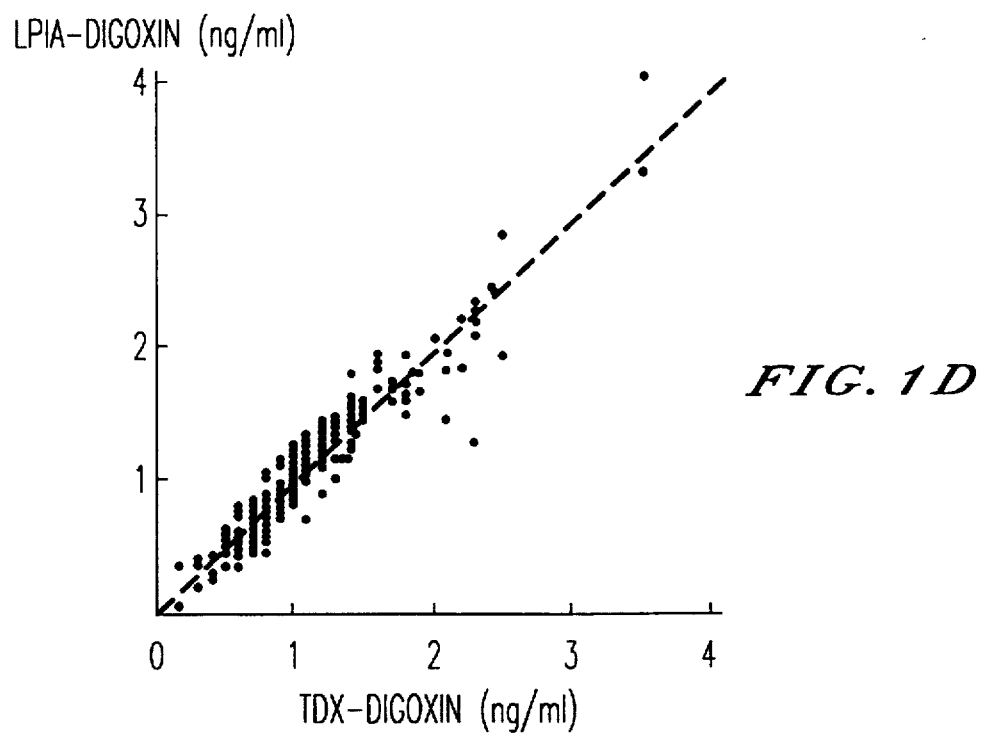

Patient serum specimens previously evaluated with $TD_x$ (Abbot) for digoxin concentration were tested using the above microparticle reagent and buffer reagent in a latex agglutination inhibition assay using the four instruments described above. The data obtained with the four above-described instruments was plotted against the results obtained by the $TD_x$ method and analyzed. FIG. 1a shows the results obtained with COBAS FARA instrument. FIG. 1b shows the results obtained with the COBAS MIRA instrument. FIG. 1c shows the results obtained with the Hitachi 704 instrument. FIG. 1d shows the results obtained with of LPIA-100 instrument.

As FIGS. 1a–d show, the latex agglutination inhibition assay conducted with reagents according to the present invention provide excellent results. The results obtained with the present invention reagents are clearly as good as, or better than, results obtained with the $TD_x$ system.

Example 2

With the same systems described above, a precision study was conducted using BioRad quality control serum or Roche calibrators. As shown by the data in Table 1, the present invention reagents provide far better precision than the currently accepted standard of 10% Coefficient of Variation (C.V.) at 1 ng/ml.

TABLE 1

10 Day Study
3 Conc Values
n = 10 Assays/Value/Day

| | 0.5 ng/mL | | 2.0 ng/mL | | 4.0 ng/mL | |
|---|---|---|---|---|---|---|
| Run-to-Run: | X | CV % | X | CV % | X | CV% |
| Day 1 | 0.546 | 7.38 | 1.968 | 4.14 | 3.985 | 2.16 |
| Day 2 | 0.542 | 5.97 | 1.939 | 2.95 | 3.973 | 1.54 |
| Day 3 | 0.515 | 4.54 | 1.868 | 2.68 | 3.973 | 1.76 |
| Day 4 | 0.493 | 6.01 | 1.869 | 3.25 | 4.038 | 2.53 |
| Day 5 | 0.491 | 8.16 | 1.934 | 3.61 | 4.103 | 1.14 |
| Day 6 | 0.559 | 5.78 | 2.017 | 3.48 | 4.228 | 2.08 |
| Day 7 | 0.581 | 5.18 | 1.957 | 3.89 | 4.034 | 1.19 |
| Day 8 | 0.635 | 6.94 | 2.012 | 1.83 | 4.152 | 3.08 |

TABLE 1-continued

| | 10 Day Study<br>3 Conc Values<br>n = 10 Assays/Value/Day | | | | | |
|---|---|---|---|---|---|---|
| | 0.5 ng/mL | | 2.0 ng/mL | | 4.0 ng/mL | |
| Run-to-Run: | X | CV % | X | CV % | X | CV% |
| Day 9 | 0.634 | 6.71 | 1.987 | 2.89 | 4.092 | 1.04 |
| Day 10 | 0.633 | 6.88 | 1.992 | 3.84 | 4.216 | 1.98 |
| Day-to-Day<br>(10 Days) | 0.563 | 9.5 | 1.963 | 3.37 | 4.079 | 2.22 |

Example 3

Figure 2:
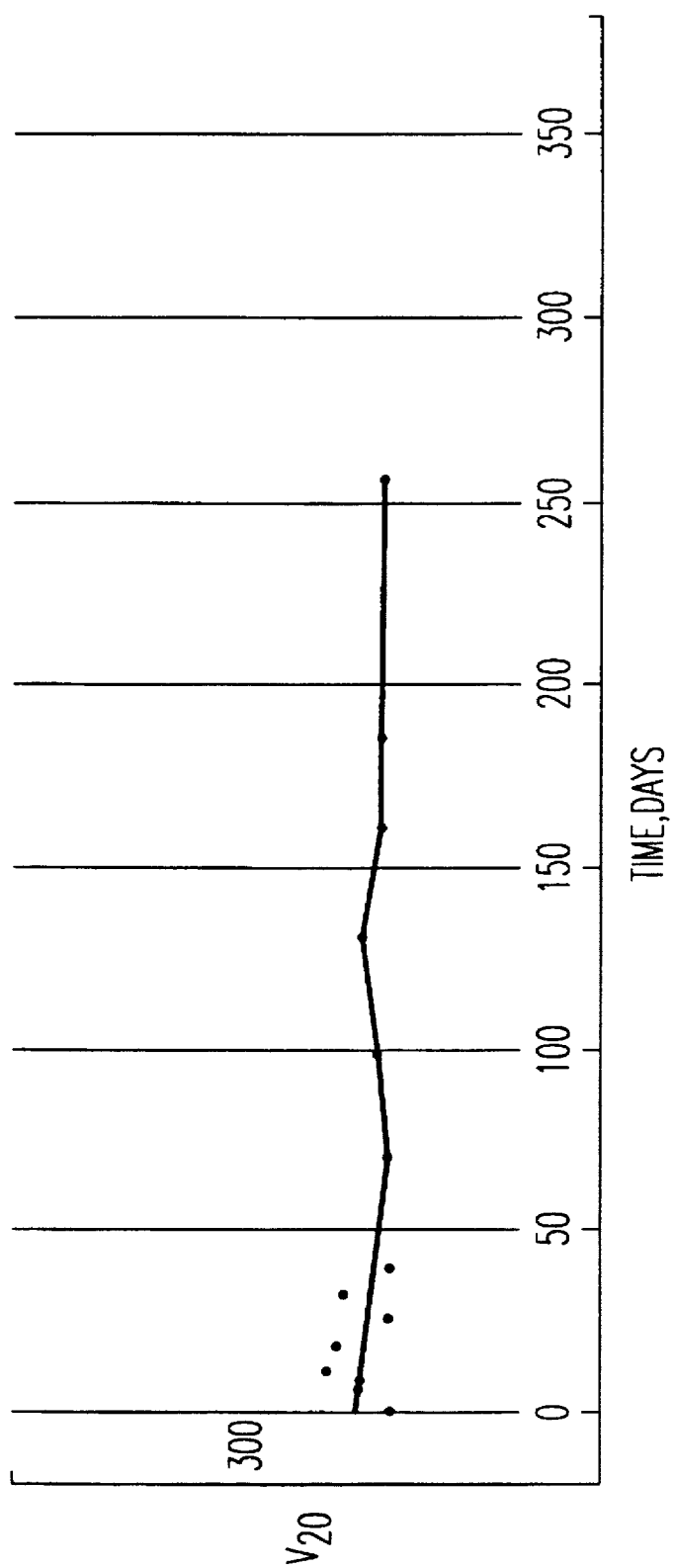
FIG. 2 shows the long term stability of the present invention digoxin sensitized microparticle reagent and antibody buffer reagent.

Using Seradyn's LPIA-100 system, the long term stability of the present invention reagents was evaluated. All reagents and calibrators were stored at 4° C. Measurements were conducted as follows: the serum sample and anti-digoxin antibody-containing buffer are incubated at 37° C. for ten minutes. Upon completion of the incubation, a digoxin conjugated latex reagent is added to bind to unoccupied antibody binding sites. The rate of agglutination reaction is measured by the increase in absorbance at 950 nm and the reaction rate over a 5 minute absorbance measurement ($V_{20}$) was plotted versus time in days in FIG. 2. As shown by the results in FIG. 2, the reagents were stable for at least nine months.

Example 4

Digoxin latex-based microparticle reagents having diameters of 0.296 μm and 0.434 μm were prepared according to the above-described protocol. 35 patient samples previously evaluated for digoxin concentration by TDx were measured in a latex-agglutination inhibition assay using the LPIA-100 system. FIGS. 3a–3d, where FIGS. 3a and 3b refer to 0.296 μm particles and 3c and 3d refer to 0.434 μm particles, show the results.

Figure 3A:
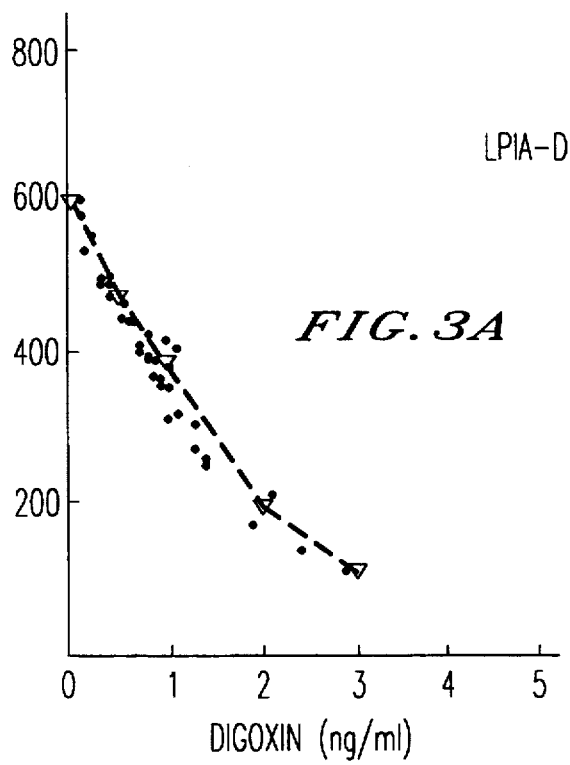
FIGS. 3a–d show the results of a digoxin assay using the LPIA-100 system using 0.296 μm particles (FIG. 3a and 3c) and 0.434 μm particles (FIG. 3b and 3d).
Figure 3B:
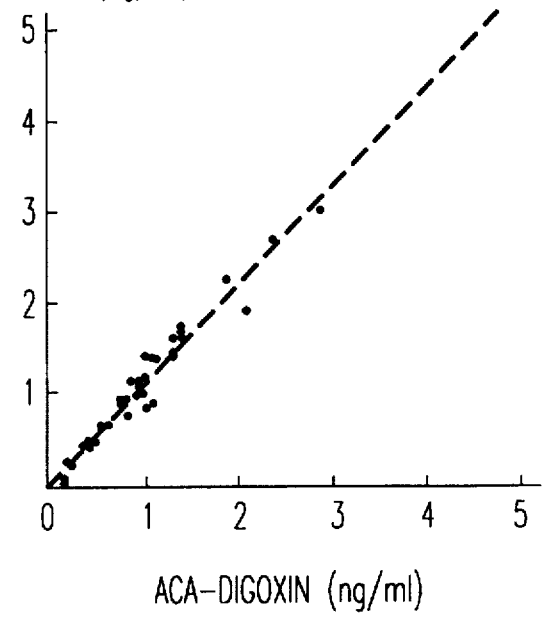
Figure 3C:
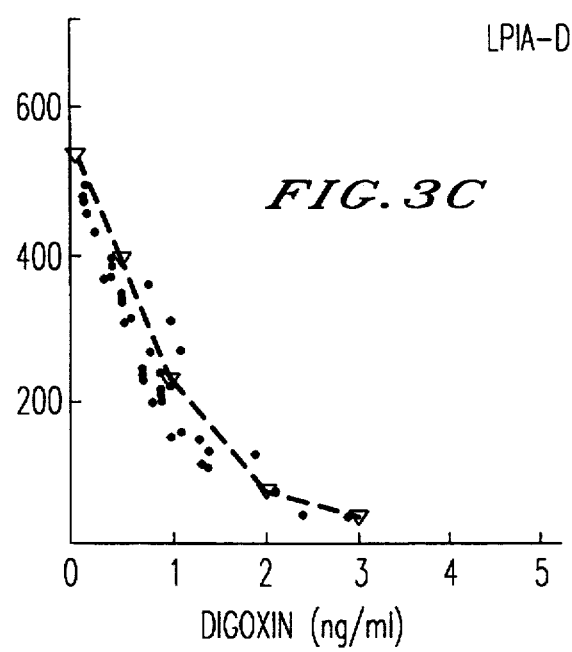
Figure 3D:
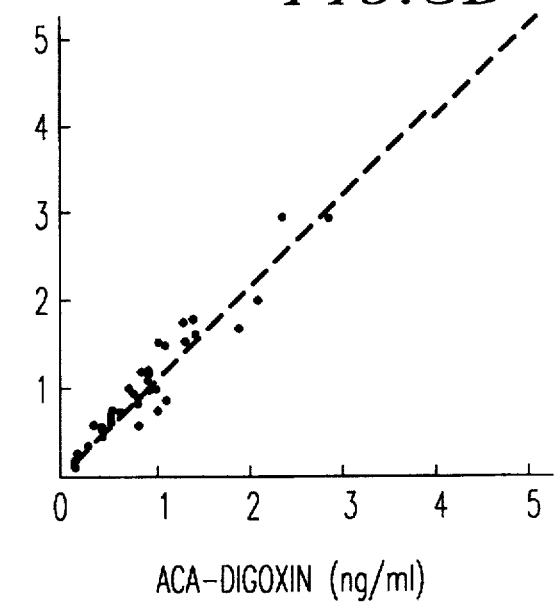

FIGS. 3a and 3c are plots of LPIA-100 rate date versus digoxin concentration as determined by DuPont ACA®; FIGS. 3b and 3d are plots of sample digoxin concentration of the same samples as determined by the LPIA-100 system (y axis) versus DuPont ACA®.

Example 5

A digoxin microparticle reagent was prepared according to the protocol above but having a 0.184 μm diameter. Using the LPIA-100 instrument with a 20 μm sample volume and the following antibody buffer system:

| 0.9 or 3.5% | Sodium Chloride |
|---|---|
| 0 or 4% | Choline Chloride |
| 200 mM | Tris-(hydroxymethyl)amino methane, pH 7.5 |
| 1.2–1.3% | Sodium Dextransulfate |
| 1 mg/ml bovine | Serum albumin |
| 0.05% | Sodium azide |
| 1:40,000 | Diluted anti-digoxin monoclonal antibody |

30 patient samples were evaluated for digoxin concentration. FIGS. 4a and 4b show the results obtained with 0.9 and 3.5% sodium chloride, respectively (using 0% choline chloride), and FIGS. 5a and 5b show the results obtained with 0 and 4% choline chloride, respectively, using 3.5% sodium chloride.

Example 6

A digoxin-sensitized microparticle reagent was prepared according to the above protocol but having a diameter of 0.292 μm and 35 patient samples were evaluated with the LPIA-100 system using 10 μl sample volumes. The antibody buffer composition used was a follows:

| 3.5% | Sodium Chloride |
|---|---|
| 250 mM | Sodium acetate, pH 5.5–7.5 |
| 0.16% | Methyl cellulose |
| 0.1–4% | Fatty-acid-free-HSA |
| 250 mM | 1-ethyl-3-(3-dimethyl-aminopropyl-urea) |
| 0.05% | Sodium azide |
| 1:60,000 | Diluted anti-digoxin monoclonal antibody |

The results are presented in FIGS. 6a–d where 6a is a control using 1.25 mg/ml FAF-HSA and with FIGS. 6b, 6c and 6d using 10, 20 and 40 mg/ml of FAF-HSA respectively.

What is claimed is:

1. A kit comprising two components A and B, component A comprising an immunoreactant immobilized on a solid support, component B comprising a buffer composition comprising a buffering agent, sodium chloride, choline chloride, a polysaccharide, fatty-acid-free serum albumin and a non-specific reaction suppressor of the formula:

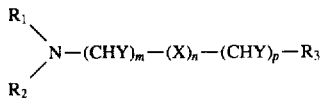

wherein X is —NH—(CO)—NH—, —NH—(CS)—NH—, or —N=C=N—, $R_1$ and $R_2$, which may be the same or different, are $C_1$–$C_5$ linear or branched alkyl groups, or $R_1$ and $R^2$, together with nitrogen, is

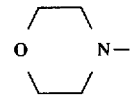

or the metho-p-toluenesulfonate salt thereof,

Y, which may be the same or different, is any of H, OH and halogen, $R_3$ is —$NR_1R_2$, —$NH_2$, —CHY, cyclohexyl, or H, m is an integer of from 2 to 5, p is an integer of from 0 to 5, and n is 0 or 1, and the acid addition salts thereof.

2. The kit according to claim 1, wherein said solid support is a latex-based carboxylate-modified particle having a diameter of from 0.18–0.5 μm.

3. The kit according to claim 1, wherein said non-specific reaction suppressor is 1-ethyl-3-(3-dimethylaminopropyl)-urea.

4. The kit according to claim 1, wherein said buffer composition further comprises water, 1.0–5.0 percent by weight sodium chloride, 1–15 percent by weight choline chloride, and either 0.2–0.3 percent by weight sodium dextran-sulfate or 0.05–1.0 percent by weight methyl cellulose as said polysaccharide, said percentages by weight based on the total weight of the buffer, and 5–100 mg/ml of fatty-acid-free human serum albumin based on the total volume of the buffer.

5. The kit according to claim 4, wherein said buffer comprises 0.1–300 mM of said non-specific reaction suppressor.

6. The kit according to claim 5, wherein said non-specific reaction suppressor is 1-ethyl-3-(3-dimethylaminopropyl)-urea.

7. The kit according to claim 5, wherein said solid support is a carboxylate-modified latex particle having a diameter of from 0.18–0.5 μm, a 10–30 square angstrom parking area, and wherein said immunoreactant is covalently bound to said particle.

8. The kit according to claim 7, wherein said immunoreactant is a digoxin-human serum albumin conjugate which has been covalently bound to said particle in a condensation reaction in the presence of a carbodiimide.

9. The kit according to claim 8, wherein said buffer further comprises a complementary immunoreactant which specifically binds to digoxin.

10. The kit according to claim 9, wherein said complimentary immunoreactant is an anti-digoxin monoclonal antibody.

11. The kit according to claim 7, wherein said buffer further comprises a complementary immunoreactant which specifically binds to said immunoreactant bound to said particle.

12. The kit as claimed in claim 1, wherein Y is selected from the group consisting of H, OH, Br, Cl and F.

13. An immunoassay method comprising the steps of:
mixing a sample comprising an analyte to be detected with a buffer composition comprising water, a buffering agent, sodium chloride, choline chloride, a polysaccharide, fatty-acid-free serum albumin, and a non-specific reaction suppressor of the formula

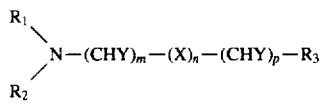

wherein X is —NH—(CO)—NH—, —NH—(CS)—NH—, or —N=C=N—, $R_1$ and $R_2$, which may be the same or different, are $C_1$–$C_5$ linear or branched alkyl groups, or $R_1$ and $R_2$, together with nitrogen, is

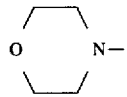

or the metho-p-toluenesulfonate salt thereof,

Y, which may be the same or different, is any of H, OH and halogen, $R_3$ is —$NR_1R_2$, —$NH_2$, —CHY, cyclohexyl, or H, m is an integer of from 2 to 5, p is an integer of from 0 to 5, and n is 0 or 1, and the acid addition salts thereof, to produce a buffer-sample mixture, contacting said buffer sample mixture with a solid support having immobilized thereon an immunoreactant which specifically reacts with said analyte to be detected so as to form a specific binding complex, and determining formation of said specific binding complex to detect said analyte.

14. The method claim 13, wherein said buffer further comprises a complementary immunoreactant which specifically binds to said immunoreactant bound to said particle.

15. The method of claim 14, wherein said buffer composition further comprises water, 1.0–5.0 percent by weight sodium chloride, 1–15 percent by weight choline chloride, and either 0.2–0.3 percent by weight sodium dextran-sulfate or 0.05–1.0 percent by weight methyl cellulose as said polysaccharide, said percentages by weight based on the total weight of the buffer, and 5–100 mg/ml of fatty-acid-free human serum albumin based on the total volume of the buffer.

16. The method of claim 13, wherein said buffer composition further comprises water, 1.0–5.0 percent by weight sodium chloride, 1–15 percent by weight choline chloride, and either 0.2–0.3 percent by weight sodium dextran-sulfate or 0.05–1.0 percent by weight methyl cellulose as said polysaccharide, said percentages by weight based on the total weight of the buffer, and 5–100 mg/ml of fatty-acid-free human serum albumin based on the total volume of the buffer.

17. The method according to claim 16, wherein said solid support is a carboxylate-modified latex particle having a diameter of from 0.18–0.50 μm, a 10–30 square angstrom parking area, and wherein said immunoreactant is covalently bound to said particle.

18. The method according to claim 15, wherein said solid support is a carboxylate-modified latex particle having a diameter of from 0.18–0.50 μm, a 10–30 square angstrom parking area, and having covalently bound thereto an immunoreactant.

19. The method of claim 13, wherein said support is a latex particle.

* * * * *

UNITED STATES PATENT AND TRADEMARK OFFICE
CERTIFICATE OF CORRECTION

PATENT NO. : 5,486,479

DATED : JANUARY 23, 1996

INVENTOR(S) : MICHIO ITO ET AL

Page 1 of 2

It is certified that error appears in the above-identified patent and that said Letters Patent is hereby corrected as shown below:

Column 2, line 3, "invention is provide" should read
--invention is to provide--;

line 52, "sodium detran-sulfate" should read
--sodium dextran-sulfate--

Column 4, line 32, "used as can mixtures" should read
--used as mixtures--.

Column 5, line 35, "The specie being" should read --The species being--

Column 7, line 35, "Fatty acid free" should read --Fatty-acid-free--;

line 42, "used to sensitized the" should read --used to sensitize the--;

line 49, "used to sensitized the" should read --used to sensitize the--.

Column 8, line 10, "and $R^2$," should read --and $R_2$,--;

line 62, "of the carbodiiminde" should read --of the carbodiimide--.

UNITED STATES PATENT AND TRADEMARK OFFICE
CERTIFICATE OF CORRECTION

PATENT NO. : 5,486,479
DATED : JANUARY 23, 1996
INVENTOR(S) : MICHIO ITO ET AL

It is certified that error appears in the above-indentified patent and that said Letters Patent is hereby corrected as shown below:

Column 9, line 44, "of specie concentration" should read --of species concentration--

Column 14, line 6, "was a follows" should read --was as follows--;
line 36, "and $R^2$," should read --and $R_2$,--.

Signed and Sealed this

Tenth Day of December, 1996

Attest:

BRUCE LEHMAN

Attesting Officer

Commissioner of Patents and Trademarks